United States Patent
Seo et al.

(10) Patent No.: US 11,052,325 B2
(45) Date of Patent: Jul. 6, 2021

(54) MEG RECOVERY APPARATUS AND MEG RECOVERY METHOD

(71) Applicant: SEOUL NATIONAL UNIVERSITY R&DB FOUNDATION, Seoul (KR)

(72) Inventors: Yutaek Seo, Seoul (KR); Hyunho Kim, Seoul (KR)

(73) Assignee: SEOUL NATIONAL UNIVERISTY OF R&DB FOUNDATION, Seoul (KR)

(*) Notice: Subject to any disclaimer, the term of this patent is extended or adjusted under 35 U.S.C. 154(b) by 235 days.

(21) Appl. No.: 16/348,777

(22) PCT Filed: Apr. 18, 2017

(86) PCT No.: PCT/KR2017/004146
§ 371 (c)(1),
(2) Date: Nov. 22, 2019

(87) PCT Pub. No.: WO2018/088650
PCT Pub. Date: May 17, 2018

(65) Prior Publication Data
US 2020/0078702 A1    Mar. 12, 2020

(30) Foreign Application Priority Data
Nov. 10, 2016 (KR) .................. 10-2016-0149810

(51) Int. Cl.
*B01D 3/14* (2006.01)
*C07C 29/80* (2006.01)
*C07C 31/20* (2006.01)

(52) U.S. Cl.
CPC .............. *B01D 3/143* (2013.01); *C07C 29/80* (2013.01); *C07C 31/202* (2013.01)

(58) Field of Classification Search
CPC ......... C07C 29/74; C07C 29/76; C07C 29/80; C07C 29/82; C07C 29/84; C07C 31/202
See application file for complete search history.

(56) References Cited

U.S. PATENT DOCUMENTS 6,340,373 B1 * 1/2002 Billington ................ B01D 1/12
23/295 R
7,232,505 B2 * 6/2007 Laborie ................... C07C 29/76
203/18

(Continued)

FOREIGN PATENT DOCUMENTS

EP    0550534 B1    9/1991
JP    4255554 B2    4/2009

(Continued)

OTHER PUBLICATIONS

Human translation of Kim et al. ("Proposal for MEG Regeneration Process Efficient Concerning Monovalent Precipitation Prevention") produced by USPTO.*

(Continued)

*Primary Examiner* — Jonathan Luke Pilcher
(74) *Attorney, Agent, or Firm* — Mayer & Williams PC; Stuart Mayer (57) ABSTRACT

Provided are a mono-ethylene glycol (MEG) recovery apparatus and a MEG recovery method. The MEG recovery apparatus includes a pretreater receiving the raw material from a raw material supplier to remove the low soluble salts, a first distiller connected to the pretreater to receive the raw material from which the low soluble salts are removed, and to form a first treated solution by vaporizing a certain amount of the water, a high soluble salt remover connected to the first distiller to remove the high soluble salts from the first treated solution, a second distiller connected to the high soluble salt remover to form a second treated solution by vaporizing the water from the first treated solution from (Continued)

which the high soluble salts are removed, and a recovery unit connected to the second distiller to recover the second treated solution.

8 Claims, 4 Drawing Sheets

(56) References Cited

U.S. PATENT DOCUMENTS

| | | | | |
|---|---|---|---|---|
| 9,006,500 | B2* | 4/2015 | Moen | C07C 29/76 |
| | | | | 568/868 |
| 9,090,813 | B2* | 7/2015 | Kaasa | C09K 8/52 |
| 9,926,250 | B2* | 3/2018 | Arumugam | B01D 21/245 |
| 2012/0018293 | A1* | 1/2012 | Kaasa | C07C 29/80 |
| | | | | 203/18 |
| 2014/0256990 | A1* | 9/2014 | Moen | B01D 1/225 |
| | | | | 568/868 |
| 2017/0129835 | A1* | 5/2017 | Arumugam | B01D 21/0012 |

FOREIGN PATENT DOCUMENTS

| | | | | |
|---|---|---|---|---|
| KR | 10152739400000 | | 6/2015 | |
| KR | 1020160001448 | | 1/2016 | |
| WO | 2015/198212 | | 6/2015 | |
| WO | WO-2015198212 A1 * | 12/2015 | | C07C 29/76 |

OTHER PUBLICATIONS

Kim et al. "Prsentation of Effective MEG Regeneration Process in Consideration of Prevention of Monovalent Salt Immersion", The Korean Society of Ocean Engineers.

* cited by examiner

FIG. 1

PRIOR ART

FIG. 2

PRIOR ART

|  | Case 1 | Case 2 | Case 3 | Case 4 |
|---|---|---|---|---|
| $Na^+$ [mg/l] | 12666 | 25575 | 33452 | 43593 |
| $Cl^-$ [mg/l] | 20046 | 40593 | 53097 | 69192 |
| $Ca^{2+}$ [mg/l] | 818 | 1665 | 2177 | 2838 |
| $HCO_3^-$ [mg/l] | 782 | 1591 | 2081 | 2712 |
| TDS [g/l] | 35 | 70 | 91 | 118 |

(b)

|  | Case 1 | | Case 2 | | Case 3 | | Case 4 | |
|---|---|---|---|---|---|---|---|---|
|  | (a) | (b) | (a) | (b) | (a) | (b) | (a) | (b) |
| MEG wt% at bottom | 90 | 75 | 90 | 75 | 90 | 75 | 90 | 75 |
| NaCl(s) depositability | X | X | X | X | O | X | O | X |

|  | $NH_4^+$ | $Li^+$ | $Na^+$ | $K^+$ | $Mg^{2+}$ | $Ca^{2+}$ | $Ba^{2+}$ | $Al^{3+}$ | $Fe^{3+}$ | $Cu^{2+}$ | $Ag^+$ | $Zn^{2+}$ | $Pb^{2+}$ |
|---|---|---|---|---|---|---|---|---|---|---|---|---|---|
| $F^-$ | sol | sol | sol | sol | insol | insol | sl sol | sol | sl sol | sol | sol | sol | insol |
| $Cl^-$ | sol | sol | sol | sol | sol | sol | sol | sol | sol | sol | insol | sol | sol |
| $Br^-$ | sol | sol | sol | sol | sol | sol | sol | sol | sol | sol | insol | sol | sl sol |
| $I^-$ | sol | sol | sol | sol | sol | sol | sol | sol |  |  | insol | sol | insol |
| $OH^-$ | sol | sol | sol | sol | insol | sl sol | sol | insol | insol | insol |  | insol | insol |
| $S^{2-}$ | sol | sol | sol | sol |  |  |  | insol | insol | insol | insol | insol | insol |
| $SO_4^{2-}$ | sol | sol | sol | sol | sol | sl sol | insol | sol | sol | sol | sl sol | sol | insol |
| $CO_3^{2-}$ | sol | sol | sol | sol | insol | insol | insol |  |  | insol |  | insol | insol |
| $NO_3^-$ | sol | sol | sol | sol | sol | sol | sol | sol | sol | sol | sol | sol | sol |
| $PO_4^{3-}$ | sol | insol | sol | sol | insol | insol | insol | insol | insol | insol | insol | insol | insol |
| $CrO_4^{2-}$ | sol | sol | sol | sol | sol | sol | insol |  | insol | insol | insol | insol | insol |
| $CH_3CO_2^-$ | sol | sol | sol | sol | sol | sol | sol | sl sol | sol | sol | sol | sol | sol | sol – soluble
insol – insoluble
sl sol – slightly soluble

MEG RECOVERY APPARATUS AND MEG RECOVERY METHOD

TECHNICAL FIELD

The present invention relates to a mono-ethylene glycol (MEG) recovery apparatus and a MEG recovery method, and more particularly, to a MEG recovery apparatus and a MEG recovery method capable of preventing deposition of high soluble salts in a distiller during a MEG recovery process and of recovering high-concentration MEG.

BACKGROUND ART

Gas hydrates are compounds formed by physical bonding due to trapping of gases, e.g., methane, ethane, and propane, into voids of water molecules in a low-temperature and high-pressure condition. In the development of deep-sea gas fields, hydrocarbons are carried to the land in a low-temperature and high-pressure condition and a risk of forming gas hydrates is high. In general, the hydrate formation condition is changed to a low-temperature and high-pressure condition by injecting a thermodynamic hydrate inhibitor.

Representative examples of the thermodynamic hydrate inhibitor include methanol and mono-ethylene glycol (MEG). Methanol is more volatile than water and is not suitable for gas fields, and thus MEG is generally used as the thermodynamic inhibitor for gas fields. MEG is less volatile than water and is suitable for gas fields. However, MEG needs to be injected by a large amount to prevent formation of hydrates and is high-priced and thus reuse thereof through a recovery process is required.

MEG is the simplest divalent alcohol, is synthesized by hydration of ethylene oxide, and is odorless, colorless, sweet-tasting, and viscous. MEG may be not only used as a hydrate inhibitor in the sea and gas industry but also broadly used as antifreeze of a vehicle engine coolant, a hydraulic fluid of a hydraulic brake, a raw material of polyester fiber, and a raw material of plastic.

DETAILED DESCRIPTION OF THE INVENTION

Technical Problem

When hydrocarbons are produced at the seabed, produced water containing a large amount of salts may flow in. A mono-ethylene glycol (MEG) recovery process is a process following a gas, condensation, and water mixture solution separation process, and aims to separate MEG reusable as an inhibitor, from a mixture solution of MEG, water, and salts.

Scale of salts may be deposited during the MEG recovery process, and a serious problem such as interruption of operation may occur when the scale is severely deposited in a reboiler of a distiller. Therefore, the key of the MEG recovery process is to prevent deposition of salts by efficiently removing the salts.

The present invention provides a MEG recovery apparatus and a MEG recovery method capable of preventing deposition of high soluble salts in a distiller.

The present invention provides a MEG recovery apparatus and a MEG recovery method capable of reducing process costs and recovering high-concentration MEG.

However, the scope of the present invention is not limited thereto.

Technical Solution

According to an aspect of the present invention, there is provided an apparatus for recovering mono-ethylene glycol (MEG) from a raw material including water, the MEG, high soluble salts, and low soluble salts, the apparatus including a pretreater receiving the raw material from a raw material supplier to remove the low soluble salts, a first distiller connected to the pretreater to receive the raw material from which the low soluble salts are removed, and to form a first treated solution by vaporizing a certain amount of the water, a high soluble salt remover connected to the first distiller to remove the high soluble salts from the first treated solution, a second distiller connected to the high soluble salt remover to form a second treated solution by vaporizing the water from the first treated solution from which the high soluble salts are removed, and a recovery unit connected to the second distiller to recover the second treated solution.

The first distiller may vaporize the water in such a manner that the first treated solution has a MEG value of 60 wt % to 75 wt %.

Deposition of the high soluble salts in the first distiller may be prevented by controlling the first treated solution to have a MEG value of 60 wt % to 75 wt %.

A heating temperature of the first distiller may be higher than a boiling point of the water and may be lower than a boiling point of the MEG.

The heating temperature of the first distiller may be 100° C. to 135° C.

The second treated solution may have a MEG value of 80 wt % to 90 wt %.

The second distiller may be connected to the first distiller and the high soluble salt remover to mix the first treated solution received from the first distiller, with the second treated solution and to transfer the mixture solution to the recovery unit.

The high soluble salts may include monovalent salts, and the low soluble salts may include divalent salts.

According to an aspect of the present invention, there is provided a method of recovering mono-ethylene glycol (MEG) from a raw material including water, the MEG, high soluble salts, and low soluble salts, the method including (a) removing the low soluble salts from the raw material, (b) forming a first treated solution by vaporizing a certain amount of the water from the raw material from which the low soluble salts are removed, (c) removing the high soluble salts from the first treated solution, (d) forming a second treated solution by vaporizing the water from the first treated solution from which the high soluble salts are removed, and (e) recovering the second treated solution.

Step (b) may be performed in such a manner that the first treated solution has a MEG value of 60 wt % to 75 wt %.

Deposition of the high soluble salts may be prevented by controlling the first treated solution to have a MEG value of 60 wt % to 75 wt %.

In step (b), a heating temperature for vaporizing the water may be higher than a boiling point of the water and may be lower than a boiling point of the MEG.

The heating temperature may be 100° C. to 135° C.

The second treated solution may have a MEG value of 80 wt % to 90 wt %.

Step (e) may include mixing the first treated solution with the second treated solution and recovering the mixture solution.

The high soluble salts may include monovalent salts, and the low soluble salts include divalent salts.

Advantageous Effects

As described above, according to an embodiment of the present invention, deposition of high soluble salts in a distiller may be prevented.

In addition, process costs may be reduced and high-concentration mono-ethylene glycol (MEG) may be recovered.

However, the scope of the present invention is not limited to the above-described effects.

EXPLANATION OF REFERENCE NUMERALS

100: MEG recovery apparatus
110: Pretreater
120: First distiller
130: High soluble salt remover
140: Second distiller
150: Recovery unit Mode of the Invention The following detailed descriptions of the invention will be made with reference to the accompanying drawings illustrating specific embodiments of the invention by way of example. These embodiments will be described in detail such that the invention can be carried out by one of ordinary skill in the art. It should be understood that various embodiments of the invention are different, but are not necessarily mutually exclusive. For example, a specific shape, structure, and characteristic of an embodiment described herein may be implemented in another embodiment without departing from the scope of the invention. In addition, it should be understood that a position or placement of each component in each disclosed embodiment may be changed without departing from the scope of the invention. Accordingly, there is no intent to limit the invention to the following detailed descriptions. The scope of the invention is defined by the appended claims and encompasses all equivalents that fall within the scope of the appended claims. In the drawings, like reference numerals denote like functions, and the dimensions such as lengths, areas, and thicknesses of elements may be exaggerated for clarity.

Hereinafter, to allow one of ordinary skill in the art to easily carry out the invention, embodiments of the present invention will be described in detail with reference to the accompanying drawings.

Figure 1:
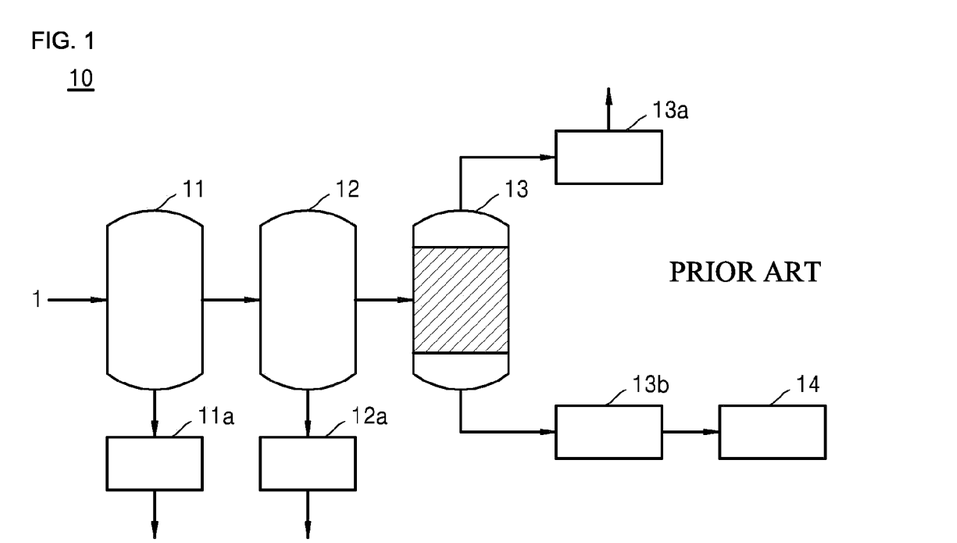
FIG. 1 is a schematic diagram of a conventional full-stream mono-ethylene glycol (MEG) recovery apparatus.
Figure 2:
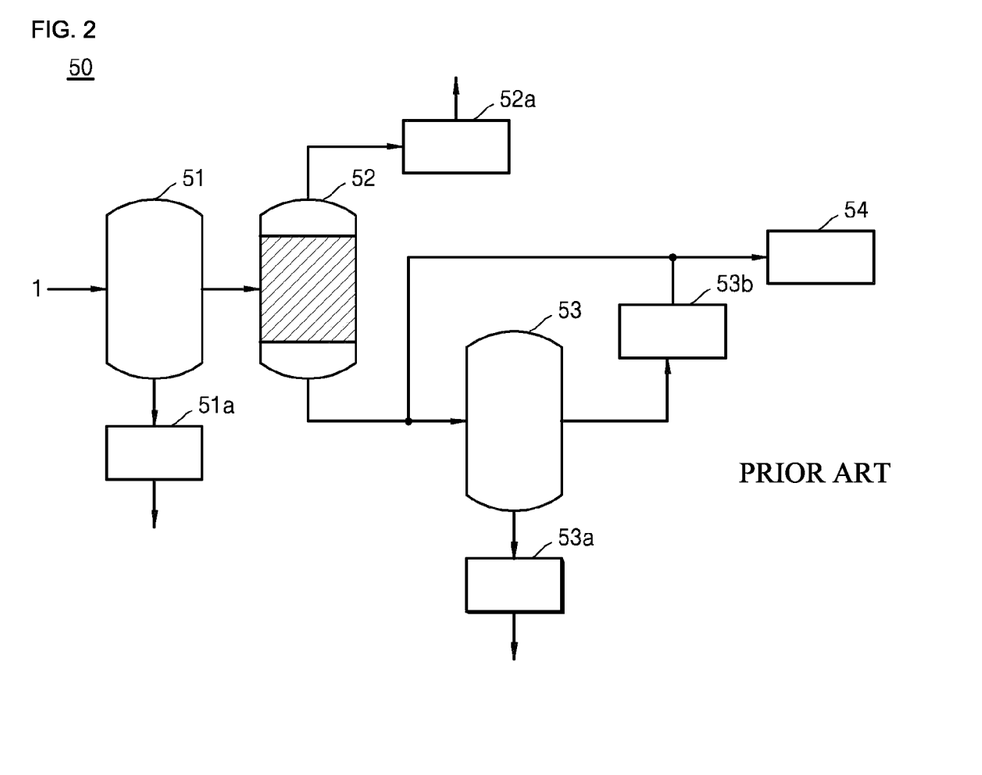
FIG. 2 is a schematic diagram of a conventional slip-stream MEG recovery apparatus.

FIG. 1 is a schematic diagram of a conventional full-stream mono-ethylene glycol (MEG) recovery apparatus 10, and FIG. 2 is a schematic diagram of a conventional slip-stream MEG recovery apparatus 50.

Referring to FIG. 1, the full-stream MEG recovery apparatus 10 includes a pretreater 11, a flash drum 12, a distiller 13, and a recovery unit 14. A full-stream MEG recovery process is as described below.

Initially, when a raw material 1 is supplied, the pretreater 11 removes some low soluble salts. The removed low soluble salts may be discharged through a low soluble salt remover 11a. Subsequently, the flash drum 12 vaporizes all water and MEG and removes high soluble salts and remaining low soluble salts. The removed salts may be discharged through a salt remover 12a. Then, the distiller 13 separates MEG from water. The water may be discharged through a water discharger 13a, and the MEG may pass through a MEG extractor 13b and be recovered as high-concentration MEG in a recovery unit 14.

In the above-described method, the flash drum 12 may consume much energy and scale of the low soluble salts may be formed on a heater of the pretreater 11. Due to the scale of the low soluble salts, operation of the heater may be interrupted and much maintenance time and costs may be required.

Referring to FIG. 2, the slip-stream MEG recovery apparatus 50 is adopted to solve the problems of the full-stream MEG recovery apparatus 10 and includes a pretreater 51, a distiller 52, a flash drum 53, and a recovery unit 54. A slip-stream MEG recovery process is as described below.

Initially, when a raw material 1 is supplied, the pretreater 51 removes low soluble salts. The removed low soluble salts may be discharged through a low soluble salt remover 51a. Subsequently, the distiller 52 separates MEG from water. The water may be discharged through a water discharger 52a. Then, a certain amount of the separated MEG is bypassed and the flash drum 53 vaporizes the bypassed MEG and removes high soluble salts. The high soluble salts may be discharged through a high soluble salt remover 53a. The MEG vaporized by the flash drum 53 may pass through a MEG extractor 53b, join a main stream of the MEG separated by the distiller 52, and be recovered as high-concentration MEG by the recovery unit 54.

In the above-described method, although energy efficiency is higher than that of the full-stream MEG recovery apparatus 10, a reboiler may be maintained at a high temperature to vaporize a large amount of the water only by the distiller 52, the high soluble salts in the separated MEG solution may be increased in concentration and be deposited in a lower or rear pipe of the distiller to form scale thereof. When the scale is accumulated, apparatus efficiency may be reduced, apparatus operation may be frequently interrupted, and thus maintenance costs may be increased. In addition, careful operation is needed not to form the scale of the high soluble salts and thus efficiency of human and material resources is reduced.

Figure 3:
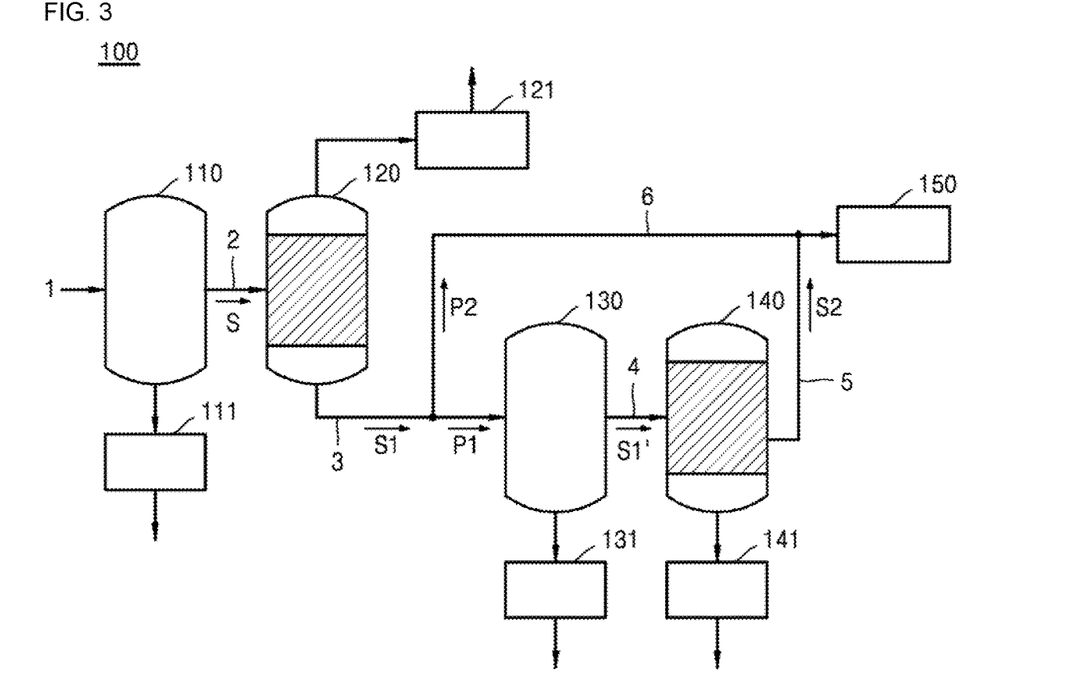
FIG. 3 is a schematic diagram of a MEG recovery apparatus according to an embodiment of the present invention.

FIG. 3 is a schematic diagram of a MEG recovery apparatus 100 according to an embodiment of the present invention.

The MEG recovery apparatus 100 of the present invention is an apparatus used in a deep-sea gas field development system to recover MEG used to inhibit formation of hydrates, and is characterized as being capable of preventing deposition of high soluble salts in a distiller and efficiently recovering high-concentration MEG.

In this regard, the MEG recovery apparatus 100 according to an embodiment of the present invention is an apparatus for recovering MEG from a raw material 1 including water, the MEG, high soluble salts, and low soluble salts, and includes a pretreater 110 receiving the raw material 1 from a raw material supplier to remove the low soluble salts, a first distiller 120 connected to the pretreater 110 to receive the raw material S from which the low soluble salts are removed, and to form a first treated solution S1 by vaporizing a certain amount of the water, a high soluble salt remover 130 connected to the first distiller 120 to remove the high soluble salts from the first treated solution S1, a second distiller 140 connected to the high soluble salt remover 130 to form a second treated solution S2 by vaporizing the water from the first treated solution S1' from which the high soluble salts are removed, and a recovery unit 150 connected to the second distiller 140 to recover the second treated solution S2.

A MEG recovery method according to an embodiment of the present invention is a method of recovering MEG from the raw material 1 including water, the MEG, high soluble salts, and low soluble salts, and includes (a) removing the low soluble salts from the raw material 1, (b) forming the first treated solution S1 by vaporizing a certain amount of the water from the raw material S from which the low soluble salts are removed, (c) removing the high soluble salts from the first treated solution S1, (d) forming the second treated solution S2 by vaporizing the water from the first treated solution S1' from which the high soluble salts are removed, and (e) recovering the second treated solution S2.

Specifically, referring to FIG. 3, the MEG recovery apparatus 100 according to an embodiment of the present invention includes the pretreater 110, the first distiller 120, the high soluble salt remover 130, the second distiller 140, and the recovery unit 150.

Figure 8:
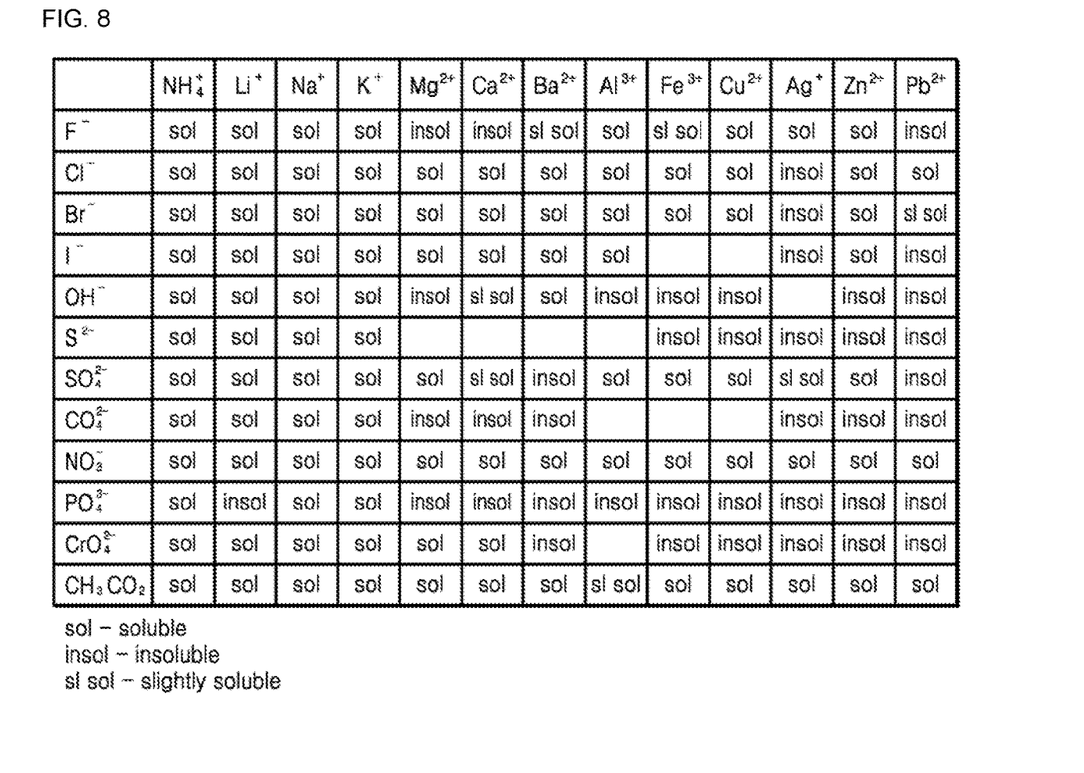
FIG. 8 is a table distinguishably showing high soluble salts and low soluble salts.

The raw material 1 may include the water, the MEG, the high soluble salts, and the low soluble salts. In this specification, the high soluble salts refer to salts that are easily soluble in water, are increased in solubility in proportion to temperature, and mainly include monovalent salts such as NaCl, KCl, and NaOH. The low soluble salts refer to salts that are not easily soluble in water, are reduced in solubility in inverse proportion to temperature, and mainly include divalent salts such as $CaCO_3$, $CaSO_4$, $BaSO_4$, and $BaCO_3$. Referring to FIG. 8, salts indicated as being "soluble" may be included in the high soluble salts, and salts indicated as being "insoluble" or "slightly soluble" may be included in the low soluble salts.

The pretreater 110 may receive the raw material 1 from a raw material supplier (not shown) to remove the low soluble salts. The pretreater 110 may include a tank (not shown) containing the raw material 1, and a heater (not shown) for heating the raw material 1. Because the low soluble salts are increased in solubility in proportion to temperature, the heater may precipitate the low soluble salts by heating the raw material 1. The precipitated low soluble salts may be discharged through a low soluble salt remover 111. The low soluble salt remover 111 may include a centrifuge (not shown), a filter (not shown), etc. to treat the low soluble salts precipitated to a solid state, and include a circulation pipe (not shown), a pump (not shown), etc. to circulate the raw material 1 back to the tank of the pretreater 110. The pretreater 110 may further employ known elements for removing low soluble salts.

The first distiller 120 may be connected to the pretreater 110 to receive the raw material (or stream) S from which the low soluble salts are removed, through a first pipe 2 and to vaporize a certain amount of the water. In this specification, a solution formed after the certain amount of the water is vaporized by the first distiller 120 is called the first treated solution S1.

The first distiller 120 may be configured as a distillation column and may evaporate and vaporize the water from the raw material S from which the low soluble salts are removed, in a fractional distillation manner. The first distiller 120 may vaporize the water at an atmospheric pressure by heating the water to a temperature higher than a boiling point of the water. However, the first distiller 120 may control the heating temperature not to vaporize an excessively large amount of the water. The vaporized water may be discharged through a water discharger 121.

As described above, according to the conventional slipstream MEG recovery apparatus 50 of FIG. 2, because the distiller 52 vaporizes a large amount of the water in a single process in such a manner that the separated MEG solution has a MEG value of about 90 wt %, the high soluble salts in the separated MEG solution may be increased in concentration and be deposited in the distiller to form scale thereof.

On the other hand, according to the present invention, the first distiller 120 may not vaporize most of the water but may vaporize only a certain amount of the water, i.e., an appropriate amount of the water, to prevent deposition of the high soluble salts. For example, the first distiller 120 may vaporize the water from the raw material S from which the low soluble salts are removed (and which has a MEG value equal to or less than 50 wt %), in such a manner that the first treated solution S1 has a MEG value of 60 wt % to 75 wt %. The amount of the water in the first treated solution S1 having a MEG value of 60 wt % to 75 wt % may prevent deposition of the high soluble salts.

The first distiller 120 should not vaporize the water by an excessively large amount in such a manner that the first treated solution S1 has a MEG value of 60 wt % to 75 wt %. In this regard, the heating temperature of the first distiller 120 may be higher than the boiling point of the water and be lower than a boiling point of the MEG. It is known that, at an atmospheric pressure, the boiling point of the water is about 100° C., the boiling point of the MEG is about 197° C., and a boiling point of the high soluble salts is equal to or higher than at least 500° C. Specifically, the heating temperature of the first distiller 120 may be 100° C. to 125° C. [see FIG. 5].

The high soluble salt remover 130 may be connected to the first distiller 120 to receive the first treated solution S1 from the first distiller 120 through a second pipe 3. The high soluble salt remover 130 may remove the high soluble salts from the first treated solution S1.

The high soluble salt remover 130 may receive a part P1 of the first treated solution S1 having passed through the second pipe 3, and then evaporate the MEG in a high-temperature and low-pressure environment. In the high-temperature and low-pressure environment, the MEG in the first treated solution S1 may be evaporated to a gaseous state and the high soluble salts may be in a sludge state. The sludge-state high soluble salts may be sent to a high soluble salt discharger 131 through a separator (not shown) of the high soluble salt remover 130 and be discharged. The gaseous-state MEG may be cooled and liquefied. The high soluble salt remover 130 may further employ known elements for removing the high soluble salts and separating the MEG.

The second distiller 140 may be connected to the high-solubility salt remover 130 to receive the first treated solution S1' from which the high soluble salts are removed, through a third pipe 4. The first treated solution S1' may be in a state from which the high soluble salts are removed to an allowable level, and mostly include the water and the MEG (e.g., 60 wt % to 75 wt %).

The second distiller 140 may additionally evaporate the water from the first treated solution S1'. The second distiller 140 may operate at a low pressure in succession to the previous process, thereby increasing energy efficiency. When the water is additionally vaporized by the second distiller 140, the second treated solution S2 including high-concentration MEG may be formed. The vaporized water may be discharged through a water discharger 141.

The second treated solution S2 may have a MEG value of about 80 wt % to 90 wt %. The second treated solution S2 may include the MEG at a higher concentration, and have a MEG value of 80 wt % to 90 wt % after being combined with a stream P2 other than the stream P1 to the high soluble salt remover 130 through the second pipe 3.

The recovery unit 150 may be connected to the second distiller 140 to recover the second treated solution S2 through a fourth pipe 5. The recovery unit 150 may recover the second treated solution S2 obtained by combining a stream of the fourth pipe 5 with the stream P2 of a fifth pipe 6 diverging from the second pipe 3.

Figure 4:
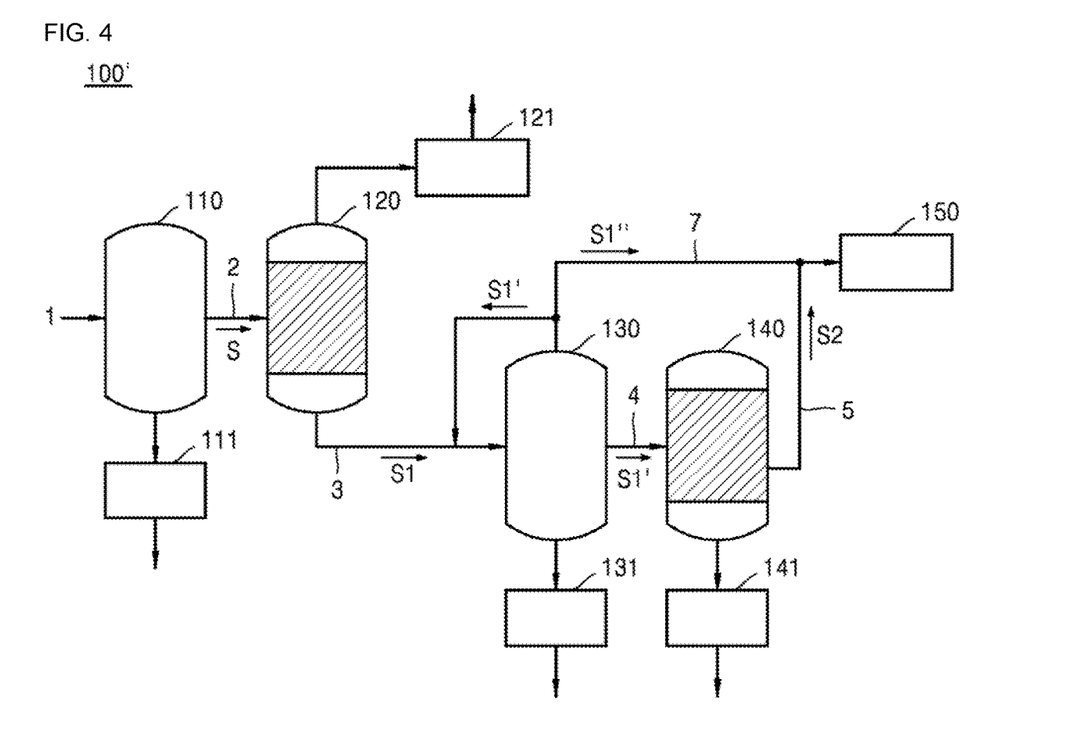
FIG. 4 is a schematic diagram of a MEG recovery apparatus according to another embodiment of the present invention.

FIG. 4 is a schematic diagram of a MEG recovery apparatus 100' according to another embodiment of the present invention. Like reference numerals in FIGS. 3 and 4 denote like elements and thus descriptions thereof will not be provided herein. The following description is focused on the differences between FIGS. 3 and 4.

Referring to FIG. 4, the second distiller 140 may be connected to the first distiller 120 and the high soluble salt remover 130. The second distiller 140 may be connected to the first distiller 120 through a sixth pipe 7, and be connected to the high soluble salt remover 130 through the third pipe 4. The second distiller 140 may mix the first treated solution S1" received from the first distiller 120, with the second treated solution S2 and transfer the mixture solution to the recovery unit 150.

Specifically, a part of the first treated solution S1' from which the high soluble salts are removed to an allowable level by the high soluble salt remover 130 may be transferred to the second distiller 140 through the third pipe 4. Another part of the first treated solution S1' treated by the high soluble salt remover 130 may return to the high soluble salt remover 130 to further remove the high soluble salts. The first treated solution S1" from which the high soluble salts are repeatedly removed is transferred through the sixth pipe 7, and this stream may be combined with the second treated solution S2 of the fourth pipe 5 and be transferred to the recovery unit 150. In this case, the amount of the recovered MEG may be reduced compared to the embodiment of FIG. 3 but increase in treatment efficiency of the high soluble salts may be expected.

According to the present invention, an appropriate amount of the water may be vaporized by the first distiller 120 to prevent deposition of the high soluble salts and thus the scale problem may be solved. Furthermore, the water may be additionally removed by the second distiller 140 after a required amount of the high soluble salts is removed, and thus high-concentration MEG may be recovered.

Although the second distiller 140 is added and thus may require additional costs compared to the conventional apparatuses, the first and second distillers 120 and 140 may be provided in small sizes due to a double distillation system and, particularly, the first distiller 120 may maintain a low process temperature and thus may greatly reduce energy consumption. Consequently, costs saved based on prevention of scale, reduction in operation interruptions/maintenances, and reduction in process energy may lead to much larger benefits compared to the addition of the second distiller 140.

Figure 5:
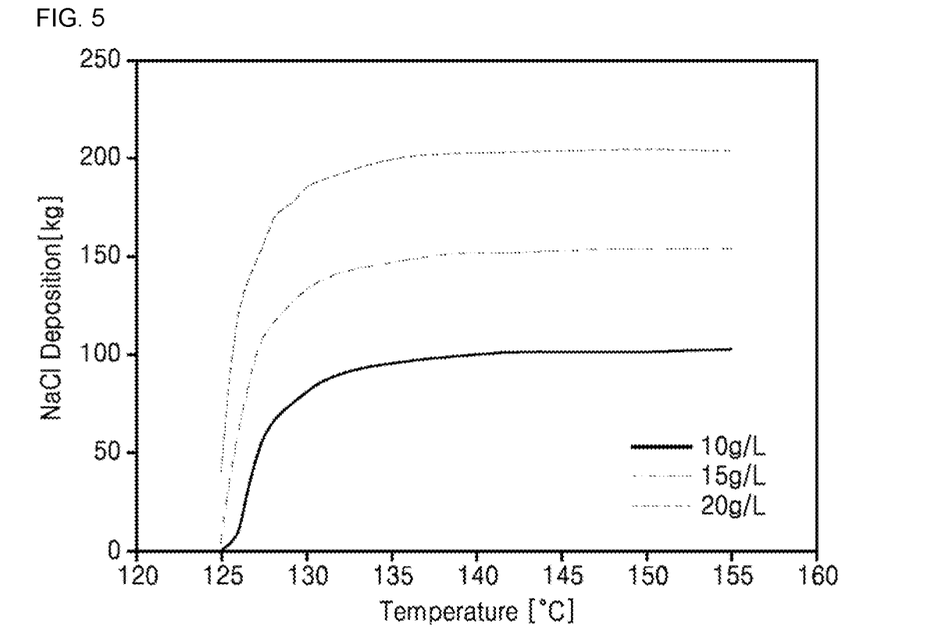
FIG. 5 is a graph showing high soluble salt deposition results in a distiller according to a simulation example using a process simulation program of the present invention.

FIG. 5 is a graph showing high soluble salt deposition results in a distiller according to a simulation example using a process simulation program of the present invention.

Operation conditions of the distiller are set as a pressure of 150 kPA, a flow rate of 10,000 kg/hr, and a MEG mixture solution having a MEG value of 50 wt %. The graph shows the amount of NaCl deposited in a reboiler based on a temperature at the bottom of the distiller when a concentration of NaCl in the MEG mixture solution varies to 10 g/L, 15 g/L, and 20 g/L.

Referring to FIG. 5, it is shown that the risk of deposition is increased in proportion to the concentration of NaCl dissolved in the MEG mixture solution, and the temperature of the reboiler. When the concentration of NaCl in the mixture solution is 10 g/L, 15 g/L, or 20 g/L, deposition occurs when the temperature of the distiller is equal to or higher than 125° C. Particularly, when the concentration of NaCl is 20 g/L, deposition occurs at 125° C. and is rapidly increased in proportion to the temperature compared to the cases when the concentration of NaCl is 10 g/L or 15 g/L. Therefore, a method of setting the heating temperature of the first distiller 120 to be lower than 125° C. may be considered to reduce deposition.

The heating temperature lower than 125° C. is a condition for recovering high-concentration MEG of 90 wt %. The heating temperature may be increased to a temperature slightly lower than the temperature corresponding to the maximum amount of deposition in FIG. 5, in such a manner that the first treated solution S1 of the first distiller 120 according to the present invention has a MEG value of 60 wt % to 75 wt %. Therefore, the heating temperature of the first distiller 120 may be set to be 100° C. to 135° C.

Figure 6:
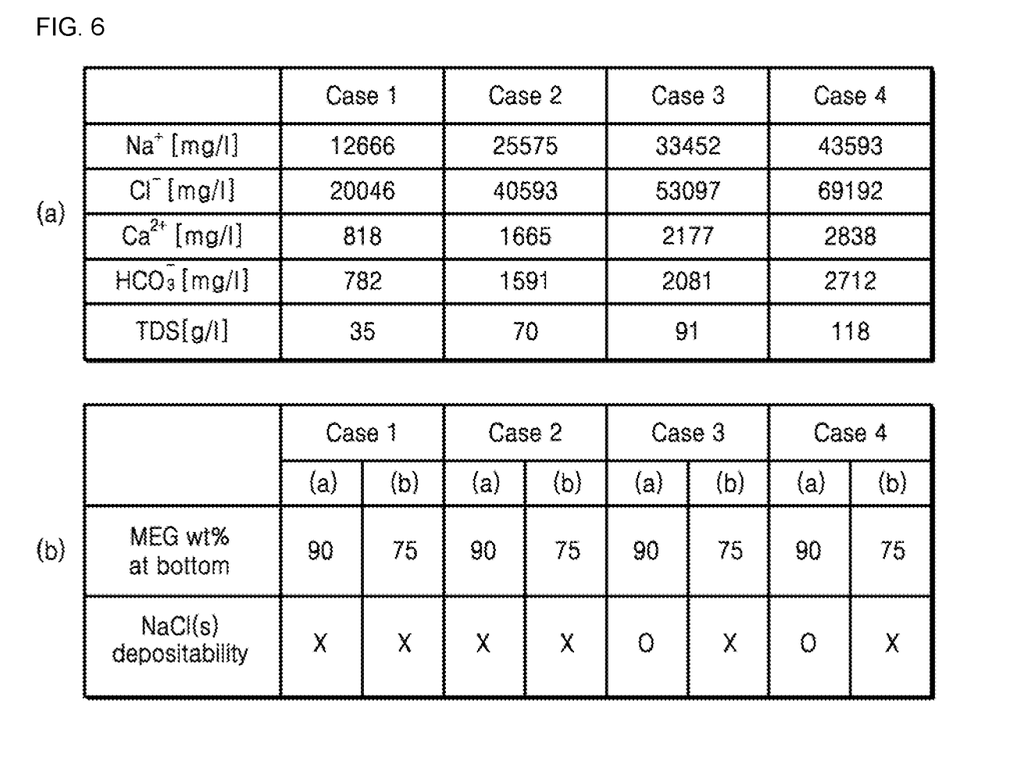
FIG. 6 includes tables showing high soluble salt deposition results in a distiller according to a comparative example and a simulation example using a process simulation program of the present invention.

FIG. 6 includes tables showing high soluble salt deposition results in a distiller according to a comparative example and a simulation example using a process simulation program of the present invention. (a) of FIG. 6 shows concentrations of salts in four types of raw materials (e.g., Cases 1 to 4), and (b) of FIG. 6 shows high soluble salt deposition results of a comparative example (a) [the conventional slip-stream MEG recovery apparatus 50 of FIG. 2] and a test example (b) [the MEG recovery apparatus 100 of FIG. 3 according to the present invention] using the four-types of the raw materials.

Referring to (b) of FIG. 6, according to the conventional technology, it is shown that depositability of NaCl is increased when the salts are included in the raw material at a high concentration. Particularly, it is shown that depositability of NaCl is increased when the concentration of total dissolved solids (TDS) is higher than 90 g/L as in Cases 3 and 4. On the other hand, according to the present invention, it is shown that NaCl is not deposited even using the raw materials of Cases 3 and 4 and thus deposition of high soluble salts is effectively prevented.

Figure 7:
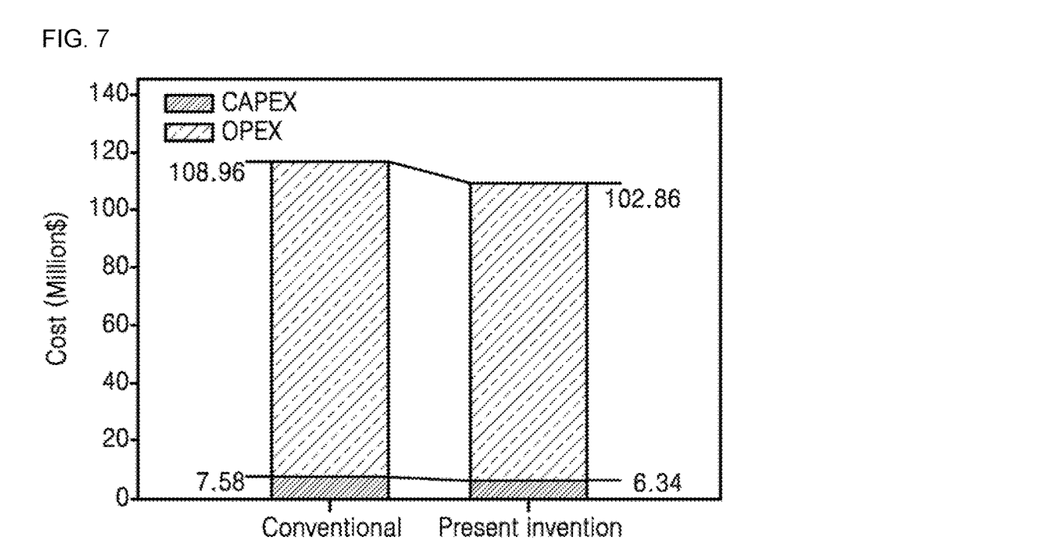
FIG. 7 is a graph showing economic evaluation results of a MEG recovery apparatus according to an embodiment of the present invention.

FIG. 7 is a graph showing economic evaluation results of a MEG recovery apparatus according to an embodiment of the present invention.

CAPEX denotes a capital expense including all expenses required to purchase and install a MEG recovery apparatus, and OPEX denotes an operating expense considering operating energy consumption for 15 years. A unit thereof is million dollars ($).

Referring to FIG. 7, a conventional technology shows a CAPEX of 7.58 and an OPEX of 108.96, and the present invention shows a CAPEX of 6.34 and an OPEX of 102.86. The conventional technology shows a total cost of 116.54 and the present invention shows a total cost of 109.20. Thus, it is shown that the total cost of the present invention is reduced by about 6.3% compared to the conventional technology.

As described above, according to the present invention, deposition of high soluble salts in a distiller may be prevented. Furthermore, process costs may be reduced and high-concentration MEG may be recovered.

While the present invention has been particularly shown and described with reference to embodiments thereof, it will be understood by one of ordinary skill in the art that various changes in form and details may be made therein without departing from the scope of the present invention as defined by the following claims.

The invention claimed is:

1. An apparatus for recovering mono-ethylene glycol (MEG) from a raw material including water, the MEG, high soluble salts, and low soluble salts, the apparatus comprising:
   a pretreater receiving the raw material from a raw material supplier to remove the low soluble salts;
   a first distiller connected to the pretreater to receive the raw material from which the low soluble salts are removed, and to form a first treated solution by vaporizing a certain amount of the water;
   a high soluble salt remover connected to the first distiller to remove the high soluble salts from the first treated solution;
   a second distiller connected to the high soluble salt remover to form a second treated solution by vaporizing the water from the first treated solution from which the high soluble salts are removed; and
   a recovery unit connected to the second distiller to recover the second treated solution.

2. The apparatus of claim 1, wherein the first distiller vaporizes the water in such a manner that the first treated solution has a MEG value of 60 wt % to 75 wt %.

3. The apparatus of claim 2, wherein deposition of the high soluble salts in the first distiller is prevented by controlling the first treated solution to have a MEG value of 60 wt % to 75 wt %.

4. The apparatus of claim 1, wherein a heating temperature of the first distiller is higher than a boiling point of the water and is lower than a boiling point of the MEG.

5. The apparatus of claim 4, wherein the heating temperature of the first distiller is 100° C. to 135° C.

6. The apparatus of claim 1, wherein the second treated solution has a MEG value of 80 wt % to 90 wt %.

7. The apparatus of claim 1, wherein the second distiller is connected to the first distiller and the high soluble salt remover to mix the first treated solution received from the first distiller, with the second treated solution and to transfer the mixture solution to the recovery unit.

8. The apparatus of claim 1, wherein the high soluble salts comprise monovalent salts, and the low soluble salts comprise divalent salts.

* * * * *

UNITED STATES PATENT AND TRADEMARK OFFICE
CERTIFICATE OF CORRECTION

| | | |
|---|---|---|
| PATENT NO. | : 11,052,325 B2 | Page 1 of 1 |
| APPLICATION NO. | : 16/348777 | |
| DATED | : July 6, 2021 | |
| INVENTOR(S) | : Yutaek Seo | |

It is certified that error appears in the above-identified patent and that said Letters Patent is hereby corrected as shown below:

On the Title Page

Item [73], insert --SEOUL NATIONAL UNIVERSITY R&DB FOUNDATION, SEOUL (KR)--

Signed and Sealed this
Fourteenth Day of February, 2023

Katherine Kelly Vidal
*Director of the United States Patent and Trademark Office*